(12) United States Patent
Zhi

(10) Patent No.: US 11,566,041 B2
(45) Date of Patent: Jan. 31, 2023

(54) NUCLEOTIDE PRODRUG COMPOUNDS

(71) Applicant: Ligand Pharmaceuticals Incorporated, Emeryville, CA (US)

(72) Inventor: Lin Zhi, Austin, TX (US)

(73) Assignee: LIGAND PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/835,828

(22) Filed: Jun. 8, 2022

(65) Prior Publication Data

US 2022/0298198 A1 Sep. 22, 2022

Related U.S. Application Data

(63) Continuation of application No. PCT/US2021/027924, filed on Apr. 19, 2021.

(60) Provisional application No. 63/013,203, filed on Apr. 21, 2020.

(51) Int. Cl.
*C07H 17/00* (2006.01)
*A61K 31/706* (2006.01)
*A61P 31/12* (2006.01)

(52) U.S. Cl.
CPC ........... *C07H 17/00* (2013.01); *A61K 31/706* (2013.01); *A61P 31/12* (2018.01)

(58) Field of Classification Search
None
See application file for complete search history.

(56) References Cited

U.S. PATENT DOCUMENTS

| | | | |
|---|---|---|---|
| 4,401,808 A | 8/1983 | Yamaji et al. | |
| 4,689,404 A | 8/1987 | Kawada et al. | |
| 4,692,434 A | 9/1987 | Hertel | |
| 4,966,891 A | 10/1990 | Morio et al. | |
| 5,476,932 A | 12/1995 | Brinkman et al. | |
| 6,312,662 B1 | 11/2001 | Erion et al. | |
| 7,456,155 B2 | 11/2008 | Sommadossi et al. | |
| 8,097,706 B2 | 1/2012 | Lee et al. | |
| 8,603,999 B2 | 12/2013 | Drummond et al. | |
| 8,653,048 B2 | 2/2014 | Xue et al. | |
| 8,741,858 B2 | 6/2014 | Ren et al. | |
| 9,447,137 B2 | 9/2016 | Suo | |
| 9,744,186 B2 | 8/2017 | Suo | |
| 10,000,521 B2 | 6/2018 | Suo et al. | |
| 10,059,733 B2 | 8/2018 | Suo et al. | |
| 10,435,429 B2 | 10/2019 | Zhi | |
| 10,899,786 B2 | 1/2021 | Cai et al. | |
| 2009/0069557 A1 | 3/2009 | Palle et al. | |

(Continued)

FOREIGN PATENT DOCUMENTS

| | | |
|---|---|---|
| CN | 1033183 | 5/1989 |
| CN | 101525361 | 9/2009 |

(Continued)

OTHER PUBLICATIONS

Almarsson et al., "Crystal Engineering of the Composition of Pharmaceutical Phases. Do Pharmaceutical Co-crystals Represent a New Path to Improved Medicines?" The Royal Society of Chemistry (2004) 1889-1896.

(Continued)

*Primary Examiner* — Layla D Berry
(74) *Attorney, Agent, or Firm* — Knobbe, Martens, Olson & Bear, LLP

(57) ABSTRACT

Provided herein are nucleotide prodrug compounds, their preparation and their uses, such as treating diseases or conditions of a viral infection.

17 Claims, 7 Drawing Sheets

(56) References Cited

U.S. PATENT DOCUMENTS

| | | |
|---|---|---|
| 2009/0221524 A1 | 9/2009 | Kotra et al. |
| 2010/0075917 A1 | 3/2010 | Decout et al. |
| 2010/0286084 A1 | 11/2010 | Ren et al. |
| 2011/0183933 A1 | 7/2011 | Guzi et al. |
| 2012/0009147 A1 | 1/2012 | Cho et al. |
| 2012/0070411 A1 | 3/2012 | Beigelman et al. |
| 2012/0088908 A1 | 4/2012 | Xue et al. |
| 2015/0224208 A1 | 8/2015 | Ueki et al. |
| 2017/0057981 A1 | 3/2017 | Chen et al. |
| 2018/0044368 A1 | 2/2018 | Zhi |
| 2019/0100551 A1 | 4/2019 | Zhi |
| 2020/0399227 A1 | 12/2020 | Zhi |
| 2021/0188887 A1 | 6/2021 | Zhi |

FOREIGN PATENT DOCUMENTS

| | | |
|---|---|---|
| CN | 101875680 | 11/2010 |
| CN | 101921303 | 12/2010 |
| CN | 102219817 | 10/2011 |
| CN | 106554382 | 4/2017 |
| EP | 0 588 317 | 3/1994 |
| EP | 0 602 454 B1 | 4/1996 |
| EP | 2 423 215 | 2/2012 |
| EP | 2 615 101 | 7/2013 |
| EP | 1 301 519 | 2/2015 |
| WO | WO 82/000293 | 2/1982 |
| WO | WO 02/008241 | 1/2002 |
| WO | WO 02/12242 | 2/2002 |
| WO | WO 05/018330 | 3/2005 |
| WO | WO 06/065525 | 6/2006 |
| WO | WO 08/030373 | 3/2008 |
| WO | WO 08/083465 | 7/2008 |
| WO | WO 08/144980 | 12/2008 |
| WO | WO 09/082846 | 7/2009 |
| WO | WO 09/106243 | 9/2009 |
| WO | WO 09/152095 | 12/2009 |
| WO | WO 10/027326 | 3/2010 |
| WO | WO 10/056403 | 5/2010 |
| WO | WO 12/031539 | 3/2012 |
| WO | WO 12/040126 | 3/2012 |
| WO | WO 13/142525 | 9/2013 |
| WO | WO 13/177195 | 11/2013 |
| WO | WO 14/032481 | 3/2014 |
| WO | WO 14/043380 | 3/2014 |
| WO | WO 14/074725 | 5/2014 |
| WO | WO 14/124430 | 8/2014 |
| WO | WO 14/145207 | 9/2014 |
| WO | WO 14/204831 | 12/2014 |
| WO | WO 15/081133 | 6/2015 |
| WO | WO 15/134334 | 9/2015 |
| WO | WO 18/091542 | 5/2018 |
| WO | WO 18/113652 | 6/2018 |
| WO | WO 19/027905 | 2/2019 |
| WO | WO 19/143860 | 7/2019 |
| WO | WO 19/169323 | 9/2019 |
| WO | WO 20/219464 | 10/2020 |

OTHER PUBLICATIONS

Bentrude et al., 1989, Efficient Preparation of Cycle 3',5'-Phosphoramidates and Amidates of Antiviral and Antitumor 5-X-2'-Deoxyuridines (X= H, CH3, I, F, CF3, trans-CH=CHBr), Nucleosides and Nucleotides, 8(7):1359-1367.

Beres et al., 1984, An Efficient Synthesis of Certain 5-Substituted-2'-Deoxyuridine 3',5'-Cyclic Monophosphate P—O-Alkyl_Aralkyl) Esters. The Crystal and Molecular Structure of 5-Iodo-2'-Deoxyuridine 3',5'-Cyclic Monophosphate P—O-methyl Ester with Axial Methoxy Group, Tetrahedron, 40(12):2405-2414.

Beres et al., 1986, Synthesis and antitumor and antiviral properties of 5-halo- and 5-(trifluoromethyl)-2'-deoxyuridine 3',5'-cyclic monophosphates and neutral triesters, J. Med. Chem., 29:1243-1249.

Chen et al., 2004, A Facile One-Pot Synthesis of N4-Alkyloxycarbonyl Cytosine Nucleosides, Synthetic Communications, 34(18):3273-3279.

Cheng et al., 2011, QSAR Models for Phosphoramidate Prodrugs of 2'-Methyicytidine as Inhibitors of Hepatitis C Virus Based on PSO Boosting, Chem Biol and Drug Design, 78:948-959.

Chou et al., "Analysis of combined drug effects: a new look at a very old problem." Trends Pharmacol Sci (1983) 4:450-454.

Chou et al., "Quantitative analysis of dose-effect relationships: the combined effects of multiple drugs or enzyme inhibitors." Adv Enzyme Regul (1984) 22:27-55.

Chou, T.C., "Theoretical basis, experimental design, and computerized simulation of synergism and antagonism in drug combination studies," Pharmacol Rev. (2006) 58(3):621-81.

Crook et al., 2014, Examining the origin of selectivity in the reaction of racemic alcohols with chiral N-phosphoryl oxazolidinones, 25:1298-1308.

DeWaziers et al., "Cytochrome P 450 Isoenzymes, Epoxide Hydrolase and Glutathione Transferases in Rat and Human Hepatic and Extraheptaic Tissues," J Pharmacol and Experimental Therapeutics (1990) vol. 253, No. 1, pp. 387-394.

Donghi et al., "Synthesis and evaluation of novel phosphoramidate prodrugs of 2'-methyl cytidine as inhibitors of hepatitis c virus NS5B polymerase," Bioorganic & Medicinal Chem Letters (2009) 19:1392-1395.

Griffiths, 2001, Cytomegalovirus, in Principles and Practice of Clinical Virology, A.J. Zuckerman et al., eds, 5th ed., pp. 85-122.

Imai et al., "Novel cell-based reporter assay system using epitope-tagged protein for the identification of agonistic ligands of constitutive androstane receptor (CAR)," Drug Metab and Phamaco (2013) 28(4):290-298.

Jain et al., "Synthesis and Study of Cyclic Pronucleotides of 5-fluoro-2'-deoxyuridine," Bioorganic and Med Chem Letters (2012) vol. 22, pp. 4497-4501.

Kawaguchi et al., 1985, Specificity of Esterases and Structure of Prodrug Esters. II. Hydrolytic Regeneration Behavior of 5-Fluro-2'-deoxyuridine (FUdR) from 3',5'-Diesters of FUdR with Rat Tissue Homogonates and Plasmain Relation to Their Antitumor Activity, Chem and Pharma Bulletin, 33(4):1652-1659.

Kotra et al., "Structure-Activity Relationships of 2'-Deoxy-2',2'difluoro-L-erythro-pentofuranosyl Nucleosides," J Med Chem (1997) 40(1):3635-3644.

Kroep et al., "Pretreatment Deoxycytidine Kinase Levels Predict in Vivo Gemcitabine Sensitivity," Mol. Cancer Ther. (2002) 1, 371-376.

LaMarche et al., Oct. 2012, Anti-hepatitis C virus activity and toxicity of type III phosphatidylinositol-4-kinase beta inhibitors, Antimicrobial Agents and Chemotherapy, 56(10): 5149-5156.

Lianzhi et al., "Synthesis of Acycionucleoside Derivatives and Analogues of 5-Fluorouracil," Nanjing Yaoxueyuan Xuebao (19896) vol. 17, No. 3, pp. 161-166.

Lohman et al., "Inactivation of lactobacillus leichmannii ribonucleotide reductase by 2',2'-difluoro-2'-deoxycitifdine 5'-triphosphate: Covalent Modification," Biochem (2010) 49(7):1404-1417..

Mackman et al., "Discovery of GS-9131: Design, synthesis and optimization of amidate prodrugs of the novel nucleoside phosphonate HIV reverse transcriptase (RT) inhibitor GS-9148," Bioorganic & Medicinal Chemistry (2010) 18:3606-3617.

Muller et al., Antiviral Strategies, 24 pp., 4 (H.-G. Krausslich et al., eds., 2009).

PUBCHEM SCHEMBLCN285547, CID: 53839260, Create Date: Dec. 4, 2011, 11 pages.

Quintiliani et al, "Design, synthesis and biological evaluation of 2'-deoxy-2',2'-diflouro-5-halouridine phosphoramidate protides," Bioorganic & Medicinal Chemistry (2011) 19(14):4338-4345.

Rautio et al., "Prodrugs: design and clinical applications," Nature Reviews Drug Discovery (2008) 7:255-270.

Saiki et al. "DCK is frequently inactivated in acquired gemcitabine-resistant human cancer cells," Biochim. Biophys. Res. Commun. (2012) 421, 98-104.

Slusarczyk et al., "Application of ProTide Technology to Gemcitabine: A Successful Approach to Overcome the Key Cancer Resistance

(56) References Cited

OTHER PUBLICATIONS

Mechanisms Leads to a New Agent (NUC-1031) in Clinical Development," J. Med. Chem. (2014) vol. 57, pp. 1531-1542.

Tanaka et al., "Chemical Synthesis of Deosyribonucleotide with a 5'-Phosphoryl Group on a Polystyrene Polymer Support by the Phosphotriester Method," Chem and Pharma Bulletin (1987)35:2726-2733.

Thornton et al., "Nucleoside Phosphate and Phosphonate Prodrug Clinical Candidates," Journal of Medicinal Chemistry (2016) 59:10400-10410.

Wilson et al., "Precursor synthesis towards the development of [1241]-labelled 2',2'-difluoro-2'deoxycytidine as a potential pet radiotracer for the anticancer drig gemicitabine," J Labelled Compounds and Radiopharmaceuticals (2001) 44(S1):S976-978.

Wu et al, "Synthesis and Biological Activity of a Gemcitabine Phosphoramidate Prodrug," J. Med Chem (2007) 50(15):3743-3746.

Zhao et al, "Synthesis and Biological Evaluation of Oral Prodrugs Based on the Structure of Gemcitabine," Chem Bio & Drug Des (2012) 80(3):479-488.

Zhuk, R., "Strucutre-Activity Relationship in Ftorafur (Tegafur) and Related 5-FU Prodrugs," Advances in Experimental and Biology (Purine and Pyrimidine Metabolism in Man IW) (1998) pp. 677-680.

Package insert for Fluorouracil injection, for intravenous use, Spectrum Pharmaceuticals, Inc., Revised Jul. 2016.

International Search Report and Written Opinion dated May 28, 2021 in application No. PCT/US2021/027924.

NUCLEOTIDE PRODRUG COMPOUNDS

CROSS REFERENCE TO RELATED APPLICATIONS

The present application is a continuation of PCT/US2021/027924, filed Apr. 19, 2021, which claims the benefit of priority to U.S. Provisional Patent Application No. 63/013,203, filed Apr. 21, 2020. Each of the foregoing applications is fully incorporated herein by reference in its entirety for all purposes.

FIELD

The present disclosure relates to the field of chemistry and medicine. More specifically, the present disclosure relates to nucleotide prodrug compounds, their preparation and their uses. In some embodiments, such compounds are useful to selectively deliver certain pharmaceutical agents to the target organs.

BACKGROUND

The following description of the background is provided to aid in understanding the invention, but is not admitted to be, or to describe, prior art.

Synthetic nucleotide analogs are widely used as antiviral or anticancer agents. Prodrug technologies have been used to improve the nucleotide molecular properties to enable the nucleotides to be more bioavailable to target organs and/or target cells, including improving oral bioavailability. Thus, new compounds with improved prodrug activation profile in addition to oral bioavailability enhancement may significantly improve the therapeutic benefits of nucleotide analog based therapies.

SUMMARY

Novel nucleotide prodrug compounds, their preparation and their uses are described. Some embodiments are novel nucleotide prodrug compounds that are delivered orally to the target organs where the compounds provide a therapeutic benefit. Additional embodiments include novel nucleotide prodrug compounds that treat a disease, disorder or condition including: hepatitis, malaria, viral infection, parasitic infection, and coronavirus infection. Another aspect includes the use of the nucleotide prodrug compounds to treat diseases that benefit from enhanced drug distribution to the target organs and like tissues and cells. In another aspect, the nucleotide prodrug compounds are used to increase the pharmacological or clinical activity of certain classes of pharmaceutical compounds such as nucleotide derived analog compounds. In some embodiments, the nucleotide prodrug compounds are useful in the more efficient oral and/or inhalation delivery of the nucleotide compounds to the target organs and cells. Some additional embodiments relate to a method of making the nucleotide prodrug compounds.

Some embodiments provided herein include a compound of Formula I:

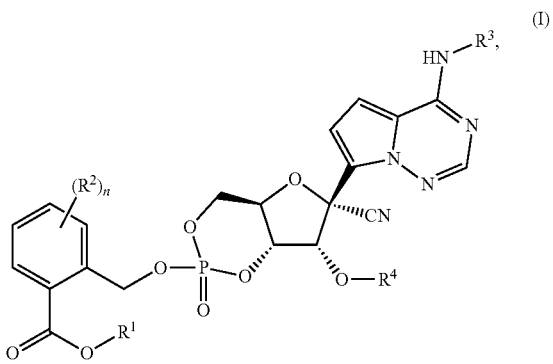

or a stereoisomer or a pharmaceutically acceptable salt thereof,
wherein $R^1$, $R^2$, $R^3$, $R^4$, and n have any of the values described herein.

Some embodiments relate to a pharmaceutical composition comprising one or more of the above compounds and a pharmaceutically acceptable excipient(s).

Some embodiments relate to a pharmaceutical composition comprising one of the above compounds and a pharmaceutically acceptable excipient(s).

Some embodiments relate to a method of treating a disease, disorder or condition comprising administering an effective amount of one of the above compounds.

In some embodiments, the disease, disorder or condition is a disease, disorder or condition of viral infection.

Some embodiments relate to a method of treating a viral infection comprising administering an effective amount of one of the above compounds to a subject in need thereof.

Some embodiments further comprise administering an effective amount of at least one additional therapeutic agent to the subject in need thereof.

In some embodiments, the subject is a mammal.
In some embodiments, the subject is human.
In some embodiments, the cell is in vivo.
In some embodiments, the cell is ex vivo.
In some embodiments, the cell is a hepatocyte.
In some embodiments, the cell is a mammalian cell.
In some embodiments, the cell is a human cell.

Some embodiments of the compounds, compositions, and methods provided herein include a pharmaceutical composition comprising one of the compounds provided herein and a pharmaceutically acceptable excipient(s).

Some embodiments of the compounds, compositions, and methods provided herein include a method of treating a disease or condition of the viral infection in a subject comprising administering an effective amount of one of the compounds provided herein to a subject in need thereof.

Some embodiments of the compounds, compositions, and methods provided herein include a method of treating a disease or condition in a subject comprising administering an effective amount of one of the compounds provided herein to a subject in need thereof.

Some embodiments also include administering an effective amount of one or more additional therapeutic agents to the subject in need thereof.

In some embodiments, the subject is a mammal.
In some embodiments, the subject is a human.

Some embodiments also include the use of one of the compounds provided herein in combination with an additional therapeutic agent.

Some embodiments of the compounds, compositions, and methods provided herein include one of the compositions provided herein for use in the preparation of a medicament for treating a disease or condition in the viral infection.

DETAILED DESCRIPTION

Figure 1:
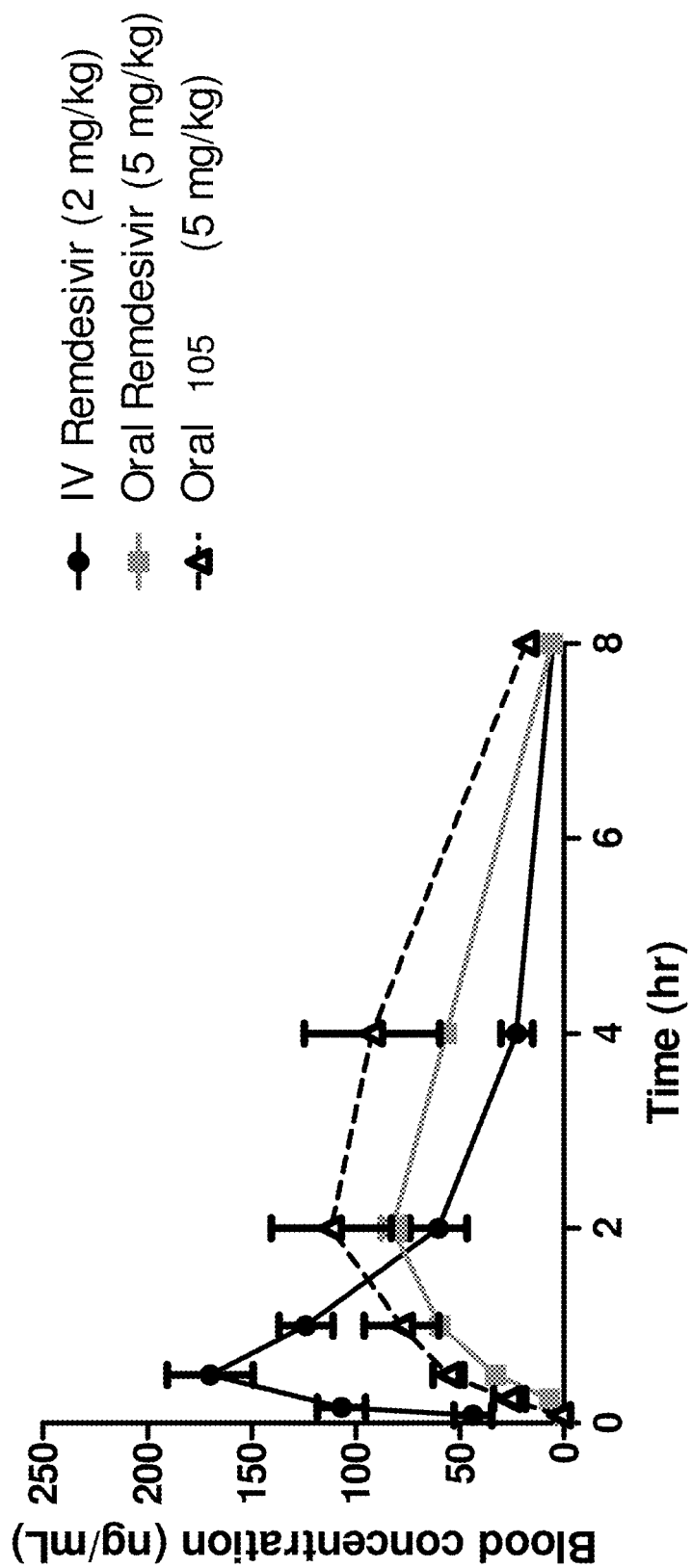
FIG. 1 is a graph showing the blood concentrations in rats of the corresponding nucleoside at selected time points after administration of IV Remdesivir, oral Remdesivir, or oral Compound 105.

The present embodiments are directed to compositions and methods related to novel nucleotide prodrug compounds, their preparation and their uses. In some embodiments, the novel nucleotide prodrug compounds facilitate delivery into cells of nucleotide derived agents, such as ribonucleotides and deoxyribonucleotides that contain nucleobase derivatives/analogs and prodrugs.

These nucleotide prodrug compounds and their stereoisomers and pharmaceutically acceptable salts are represented by Formula I:

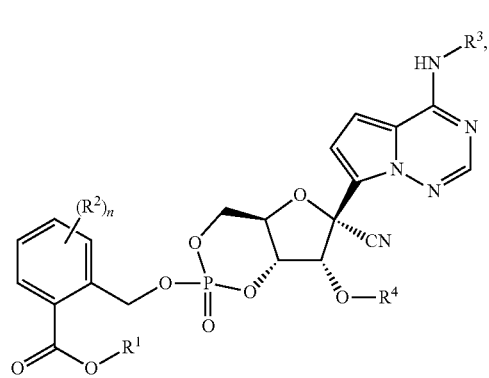

or a stereoisomer or a pharmaceutically acceptable salt thereof, wherein $R^1$, $R^2$, $R^3$, $R^4$, and n have any of the values described herein.

In some embodiments, $R^1$ is selected from a group of H, an optionally substituted $C_1$-$C_{15}$ alkyl, an optionally substituted $C_3$-$C_{15}$ cycloalkyl, and an optionally substituted $C_2$-$C_{15}$ alkenyl.

In some embodiments, $R^1$ is an optionally substituted $C_1$-$C_{15}$ alkyl.

In some embodiments, $R^1$ is an unsubstituted $C_1$-$C_6$ alkyl.

In some embodiments, $R^1$ is ethyl.

In some embodiments, $R^1$ is n-propyl.

In some embodiments, $R^1$ is i-propyl.

In some embodiments, $R^1$ is methyl.

In some embodiments, $R^2$ is selected from a group of halogen, an optionally substituted alkyl, and an optionally substituted alkyloxy.

In some embodiments, $R^3$ is selected from a group of H, an optionally substituted acyl, and C-carboxy.

In some embodiments, $R^3$ is H.

In some embodiments, $R^4$ is selected from a group of H, an optionally substituted acyl, C-amido, and C-carboxy.

In some embodiments, n is 0, 1, 2, or 3.

In some embodiments, n is 0.

In some embodiments, n is 1.

In some embodiments, $R^4$ is C-carboxy. In some embodiments, $R^4$ is acyl.

In some embodiments, the compound is selected from the group consisting of:

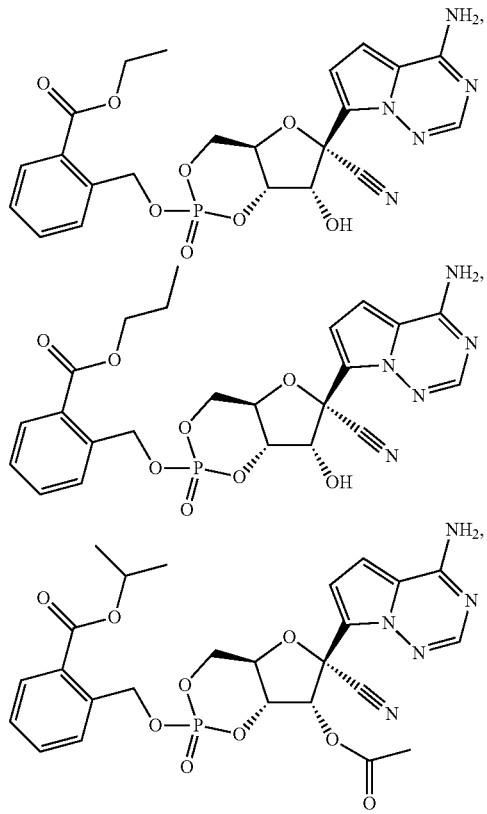

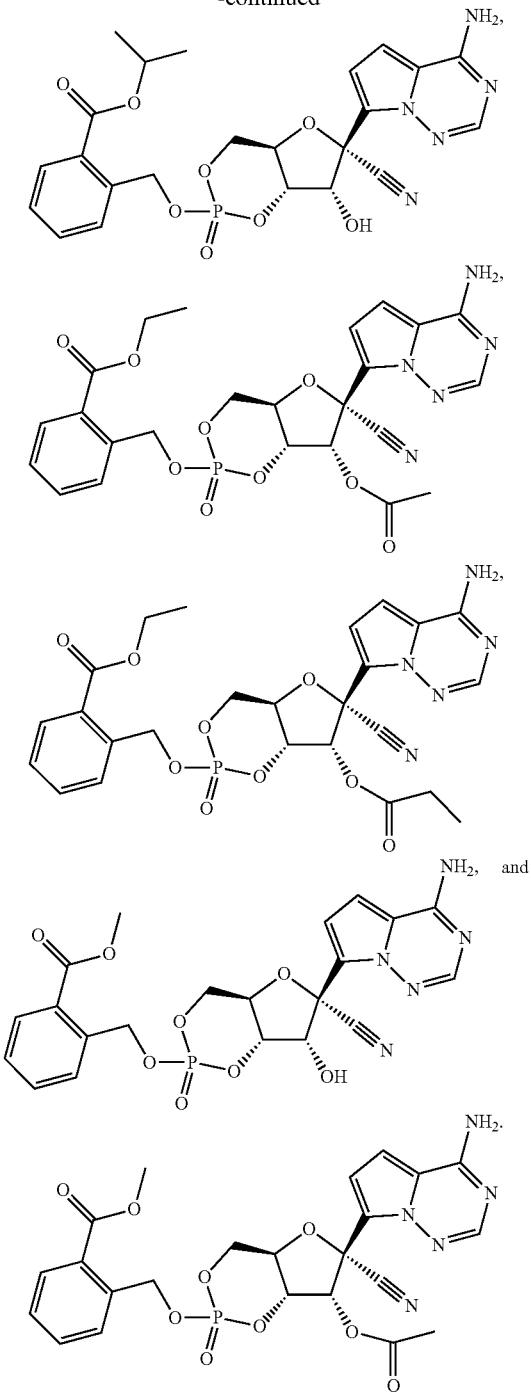

In some embodiments, the nucleotide prodrug compounds of Formula I are substrates of enzymes such as cytochrome p450 isozymes CYP3As (a family of monooxygenase), dehydrogenases, esterases, and amidases.

In some embodiments, the compound is activated within a cell upon cleavage of the prodrug moieties, releasing an active form of the compound.

In some embodiments, the disclosed compounds are used to improve pharmacokinetic properties such as prolonging half-life or enhancing absorption of a nucleotide. In addition, the disclosed methodology can be used to achieve sustained delivery of a biologically relevant nucleotide. Due to the pharmacokinetic property enhancement of the nucleotide prodrug compounds of Formula I, the compounds are used to treat diseases or conditions of a viral infection. In some embodiments, a method of making these compounds is described.

The compounds of Formula I have asymmetric centers where the stereochemistry may be unspecified, and the diastereomeric mixtures of these compounds are included, as well as the individual stereoisomers when referring to a compound of Formula I generally.

In some embodiments, an effective amount of a disclosed compound is used to treat a disease, disorder, or condition in a subject in need thereof.

In some embodiments, the compounds described herein are used to treat a viral infection.

In some embodiments, the compounds described herein are used in combination with one or more additional therapeutic agents.

In some embodiments, the compounds described herein are used in the preparation of a medicament for treating a viral infection.

In some embodiments, the compounds described herein are used in a method of treating a viral infection comprising administering an effective amount of the compounds to a subject in need thereof.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

In some embodiments, the subject is mammalian.

In some embodiments, the subject is human.

Some embodiments of the compounds, compositions and methods provided herein include a method of testing a compound in a cell comprising contacting the cell with the disclosed compounds.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

In accordance with the present disclosure and as used herein, the following terms are defined with the following meanings, unless explicitly stated otherwise. It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycle (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl(mercapto), halo($C_1$-$C_6$)alkyl (e.g., $-CF_3$), halo($C_1$-$C_6$)alkoxy (e.g., $-OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "heteroacyl" refers to —C(=O)R, wherein R is a $C_{1-6}$ heteroalkyl.

An "alkyloxymethylene" refers to —CH$_2$OR, wherein R is a $C_{1-6}$ alkyl, or heteroalkyl, all optionally substituted.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_2$-6 alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

The term "acyloxy" refers to —OC(O)R where R is alkyl.

The term "alkoxy" or "alkyloxy" refers to OR where R is alkyl, or heteroalkyl, all optionally substituted.

The term "carboxyl" refers to a C(O)OH.

The term "oxo" refers to an =O group.

The term "halogen" or "halo" refers to F (fluoro), Cl (chloro), Br (bromo) and I (iodo).

The term "haloalkyl" refer to alkyl groups containing at least one halogen, in a further aspect are 1 to 3 haloatoms. Suitable haloatoms include F, Cl, and Br.

The term "haloacyl" refer to —C(O)-haloalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In some embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, "cycloalkyl" means a fully saturated carbocyclyl ring or ring system. Examples include cyclopropyl, cyclobutyl, cyclopentyl, and cyclohexyl. The cycloalkyl group may have 3 to 10 carbon atoms (whenever it appears herein, a numerical range such as "3 to 10" refers to each integer in the given range. The cycloalkyl group may be designated as "$C_3$-$C_8$ cycloalkyl" or similar designations. By way of example only, "$C_3$-$C_8$ cycloalkyl" indicates that there are three to eight carbon atoms in the carbocyclyl ring or ring system.

As used herein, "heterocyclyl" means a non-aromatic cyclic ring or ring structure that is fully saturated or partially saturated and includes at least one heteroatom selected from nitrogen, oxygen, and sulfur in the ring backbone. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocycloalkyl group may be designated as "3-15-membered heterocycloalkyl," "4-10-membered heterocycloalkyl," "3-15-membered $C_{2-14}$heterocycloalkyl," "5-9-membered $C_{4-8}$heterocycloalkyl," "5-10-membered $C_{4-9}$heterocycloalkyl," "5-membered $C_{3-4}$heterocycloalkyl," "6-membered $C_{4-5}$heterocycloalkyl," "7-membered $C_{5-6}$heterocycloalkyl," "bicyclic or tricyclic 9-15-membered $C_{8-14}$heterocycloalkyl," "monocyclic or bicyclic 3-10-membered $C_{2-9}$ heterocycloalkyl," "bicyclic 8-10-membered $C_{4-9}$ heterocycloalkyl," "bicyclic 8-10-membered $C_{5-9}$ heterocycloalkyl," "monocyclic 4-7-membered $C_{3-6}$-heterocycloalkyl," "monocyclic 5-6-membered $C_{3-5}$-heterocycloalkyl," or similar designations. The heterocyclyl group could also be a $C_2$-$C_9$ heterocyclyl having 3 to 10 ring members with from one up to three of O (oxygen), N (nitrogen) or S (sulfur). The heterocyclyl group may be designated as "3-10 membered $C_2$-$C_9$ heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen) or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

Similarly, when two "adjacent" R groups are said to form a ring "together with the atom to which they are attached," it is meant that the collective unit of the atoms, intervening bonds, and the two R groups are the recited ring. For example, when the following substructure is present:

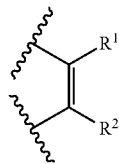

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

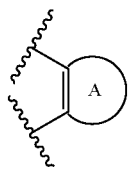

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

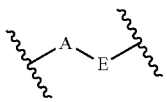

includes the substituent being oriented such that the A is attached at the leftmost attachment point of the molecule as well as the case in which A is attached at the rightmost attachment point of the molecule.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formula I derived from the combination of a compound of the present embodiments and an organic or inorganic acid or base. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, adipic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzenesulfonic acid, methanesulfonic acid, ethanesulfonic acid, p-toluenesulfonic acid, (+)-7,7-dimethyl-2-oxobicyclo[2.2.1]heptane-1-methanesulfonic acid, 1,2-ethanedisulfonic acid, dodecyl sulfonic acid, salicylic acid, glucoheptonic acid, gluconic acid, glucuronic acid, hippuric acid, hydrochloride hemiethanolic acid, 2-hydroxyethanesulfonic acid, lactic acid, lactobionic acid, methylbromide acid, methyl sulfuric acid, 2-naphthalenesulfonic acid, oleic acid, 4,4'-methylenebis-[3-hydroxy-2-naphthalenecarboxylic acid], polygalacturonic acid, stearic acid, sulfosalicylic acid, tannic acid, terphthalic acid and the like. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

The term "patient" refers to an animal being treated including a mammal, such as a dog, a cat, a cow, a horse, a sheep, and a human. In some embodiments, the patient is a mammal, either male or female. In some embodiments, the patient is a male or female human.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, HOOPR2—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are examples, not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) attached to the stereogenic centers either carbon or phosphorus atoms, and refers to individual or any combination of the individual isomers such as a racemic mixture and a diastereomeric mixture. When a compound has two stereogenic centers, there are 4 potential stereoisomers.

The term "enhanced oral bioavailability" refers to an increase of at least about 50% of the absorption of the dose of the reference drug. In an additional aspect, the increase in oral bioavailability of the compound (compared to the reference drug) is at least about 100%, or a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease).

The terms "biological agent" refers to a compound that has biological activity or that has molecular properties that can be used for therapeutic or diagnosis purposes, such as a compound carrying a radioactive isotope or a heavy atom.

The terms "molecular pathway" refers to a series of molecular events in tissues such as a receptor modulating sequence, an enzyme modulating sequence, or a biosynthesis sequence that is involved in physiological or pathophysiological functions of a living animal.

Administration and Pharmaceutical Compositions

The disclosed compounds may be used alone or in combination with other treatments. These compounds, when used in combination with other agents, may be administered as a daily dose or an appropriate fraction of the daily dose (e.g., b.i.d.). The compounds may be administered after a course of treatment by another agent, during a course of therapy with another agent, administered as part of a therapeutic regimen, or may be administered prior to therapy with another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soft gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The actual dose of the compounds described herein depends on the specific compound, and on the condition to be treated; the selection of the appropriate dose is well within the knowledge of the skilled artisan. In some embodiments, a daily dose may be from about 0.1 mg/kg to about 100 mg/kg or more of body weight, from about 0.25 mg/kg or less to about 50 mg/kg from about 0.5 mg/kg or less to about 25 mg/kg, from about 1.0 mg/kg to about 10 mg/kg of body weight. Thus, for administration to a 70 kg person, the dosage range would be from about 7 mg per day to about 7000 mg per day, from about 35 mg per day or less to about 2000 mg per day or more, from about 70 mg per day to about 1000 mg per day.

Methods of Treatment

Some embodiments of the present invention include methods of treating a disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia, a hormonal condition, HIV, and various types of cancer with the compounds, and compositions comprising compounds described herein. Some methods include administering a compound, composition, pharmaceutical composition described herein to a subject in need thereof. In some embodiments, a subject can be an animal, e.g., a mammal, a human. In some embodiments, the subject is a human.

Some embodiments provide a method of treating an infection caused by an infectious agent with an effective amount of one or more compounds as disclosed herein, wherein the infectious agent is a virus. In some embodiments, the virus is a single-stranded RNA virus. In other embodiments, the virus is a double-stranded RNA virus. In yet other embodiments, the virus is a positive-sense ssRNA virus. In some embodiments, the virus is a negative-sense ssRNA virus. In some embodiments, the virus is a double-stranded DNA virus. In other embodiments, the virus is a single-stranded DNA virus.

In some embodiments, the virus may be a coronavirus. In some embodiments, the virus may be pox virus. In some embodiments, the virus may be smallpox virus. In some embodiments, the virus may be Marburg virus. In some embodiments, the virus may be Ebola virus. In some embodiments, the virus may be flaviviruses. In some embodiments, the virus may be influenza virus. In some embodiments, the virus may be parainfluenza virus. In some embodiments, the virus may be respiratory syncytial virus. In some embodiments, the virus may be rubella virus. In some embodiments, the virus may be human immunodeficiency virus. In some embodiments, the virus may be human papillomavirus. In some embodiments, the virus may be varicella-zoster virus. In some embodiments, the virus may be herpes simplex virus. In some embodiments, the virus may be cytomegalovirus. In some embodiments, the virus may be an Epstein-Barr virus. In some embodiments, the virus may be JC virus. In some embodiments, the virus may be rhabdovirus. In some embodiments, the virus may be rotavirus. In some embodiments, the virus may be rhinovirus. In some embodiments, the virus may be adenovirus. In some embodiments, the virus may be papillomavirus. In some embodiments, the virus may be parvovirus. In some embodiments, the virus may be picornavirus. In some embodiments, the virus may be poliovirus. In some embodiments, the virus may be hantavirus. In some embodiments, the virus may be filovirus. In some embodiments, the virus may be coxsackievirus. In some embodiments, the virus may be equine encephalitis virus. In some embodiments, the virus may be a Rift Valley fever virus. In some embodiments, the virus may be an alphavirus. In some embodiments, the virus may be hepatitis A virus, hepatitis B virus, hepatitis C virus, hepatitis D virus, or hepatitis E virus.

In some embodiments, the virus may be a coronavirus. In some embodiments, the coronavirus may be MERS-CoV. In other embodiments, the coronavirus may be SARS-CoV. In some embodiments, the coronavirus may be SARS-CoV-2.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament or additional therapeutic agent(s). By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered i.v.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Synthesis of Compounds

The following procedures for the preparation of the new compounds illustrate the general procedures used to prepare the nucleotide prodrug compounds.

Scheme I describes general synthesis of the compounds of Formula I. Nucleoside (1) reacts with the phosphanediamine (2) in the presence of 4,5-dicyanoimidazole to give the cyclic product of structure 3 and the crude reaction mixture is then treated with an oxidation agent such as tert-butyl hydroperoxide to afford the final product 4 of Formula I.

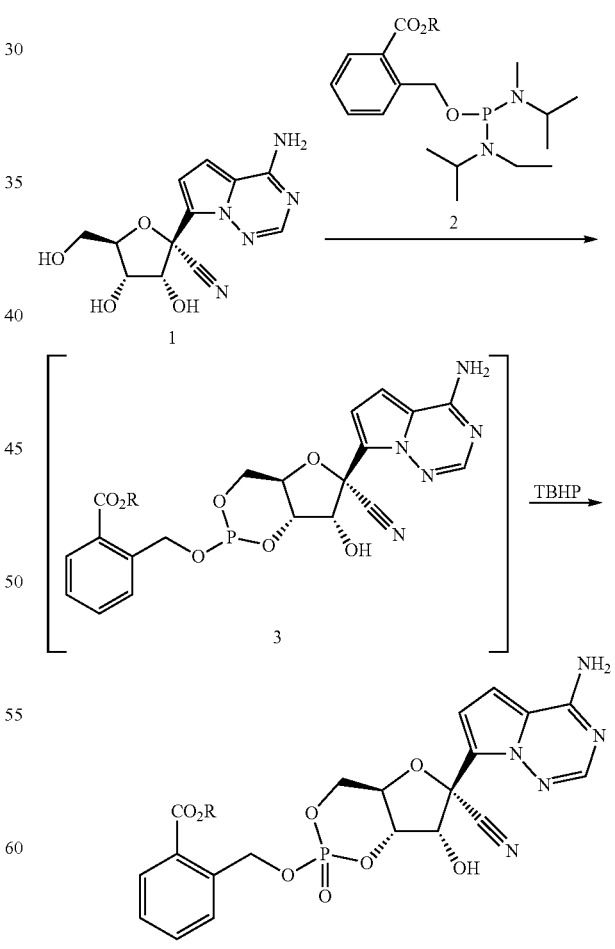

R has the definition as $R^1$ described above.

EXAMPLES

Some compounds of Formula I were prepared as outlined below.

Example 1

Ethyl 2-((((4aR,6R,7R,7aS)-6-(4-aminopyrrolo[2,1-f][1,2,4]triazin-7-yl)-6-cyano-7-hydroxy-2-oxidotetrahydro-4H-furo[3,2-d][1,3,2]dioxaphosphinin-2-yl)oxy)methyl)benzoate (Compound 101)

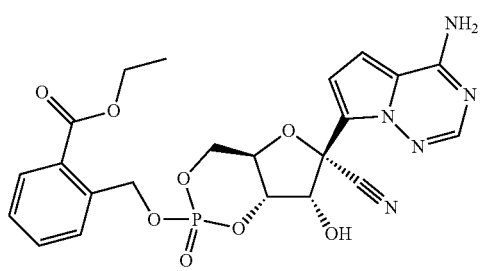

Compound 101 was prepared according to the method described in Scheme I from N,N,N',N'-tetraisopropyl-1-(2-(2-ethyloxy)carbonylbenzyloxy)phosphanediamine and (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. [M−1]$^+$ calculated for $C_{22}H_{22}N_5O_8P$: 514.11. Found: 514.1.

Example 2

Propyl 2-((((4aR,6R,7R,7aS)-6-(4-aminopyrrolo[2,1-f][1,2,4]triazin-7-yl)-6-cyano-7-hydroxy-2-oxidotetrahydro-4H-furo[3,2-d][1,3,2]dioxaphosphinin-2-yl)oxy)methyl)benzoate (Compound 102)

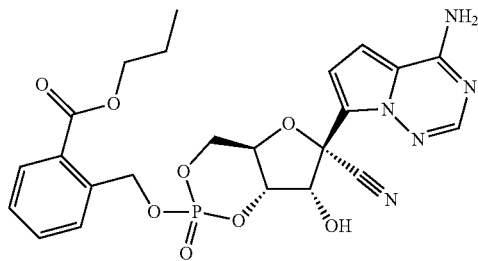

Compound 102 was prepared according to the method described in Scheme I from N,N,N',N'-tetraisopropyl-1-(2-(2-propyloxy)carbonylbenzyloxy)phosphanediamine and (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. [M−1]$^+$ calculated for $C_{23}H_{24}N_5O_8P$: 528.13. Found: 258.1.

Example 3

Isopropyl 2-((((4aR,6R,7R,7aS)-6-(4-aminopyrrolo[2,1-f][1,2,4]triazin-7-yl)-6-cyano-7-hydroxy-2-oxidotetrahydro-4H-furo[3,2-d][1,3,2]dioxaphosphinin-2-yl)oxy)methyl)benzoate (Compound 103)

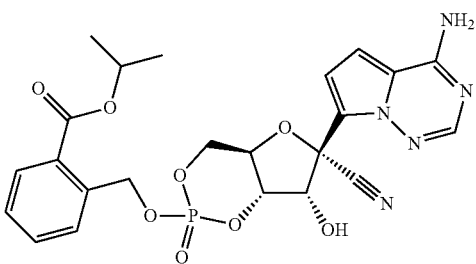

Compound 103 was prepared according to the method described in Scheme I from N,N,N',N'-tetraisopropyl-1-(2-(2-isopropyloxy)carbonylbenzyloxy)phosphanediamine and (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. [M−1]$^+$ calculated for $C_{23}H_{24}N_5O_8P$: 528.13. Found: 258.1.

Example 4

Isopropyl 2-((((4aR,6R,7R,7aR)-7-acetoxy-6-(4-aminopyrrolo[2,1-f][1,2,4]triazin-7-yl)-6-cyano-2-oxidotetrahydro-4H-furo[3,2-d][1,3,2]dioxaphosphinin-2-yl)oxy)methyl)benzoate (Compound 104)

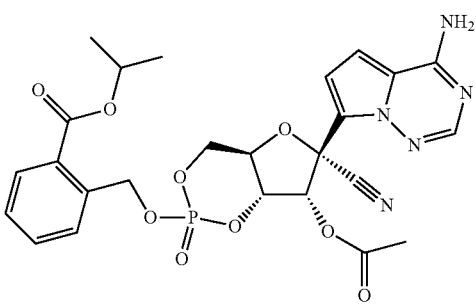

Compound 104 was prepared by standard acylation of Compound 103 with acetic anhydride in the presence of triethylamine. [M−1]$^+$ calculated for $C_{25}H_{26}N_5O_9P$: 570.14. Found: 570.1.

Example 5

Ethyl 2-((((4aR,6R,7R,7aR)-7-acetoxy-6-(4-aminopyrrolo[2,1-f][1,2,4]triazin-7-yl)-6-cyano-2-oxidotetrahydro-4H-furo[3,2-d][1,3,2]dioxaphosphinin-2-yl)oxy)methyl)benzoate (Compound 105)

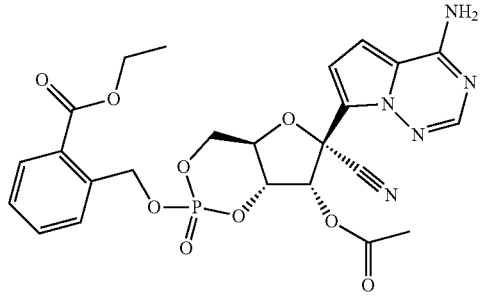

Compound 105 was prepared by standard acylation of Compound 101 with acetic anhydride in the presence of triethylamine. [M−1]⁺ calculated for $C_{24}H_{24}N_5O_9P$: 556.12. Found: 556.1.

Example 6

Ethyl 2-((((4aR,6R,7R,7aR)-6-(4-aminopyrrolo[2,1-f][1,2,4]triazin-7-yl)-6-cyano-2-oxido-7-(propionyloxy)tetrahydro-4H-furo[3,2-d][1,3,2]dioxaphosphinin-2-yl)oxy)methyl)benzoate (Compound 106)

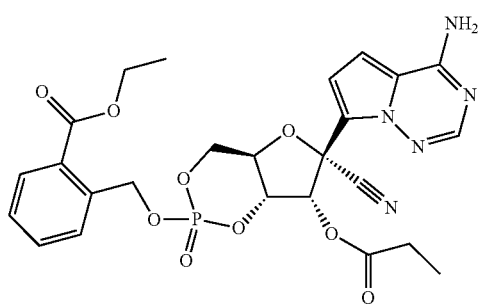

Compound 106 was prepared by standard acylation of Compound 101 with propionic anhydride in the presence of triethylamine. [M−1]⁺ calculated for $C_{25}H_{26}N_5O_9P$: 570.14. Found: 570.1.

Example 7

Methyl 2-((((4aR,6R,7R,7aS)-6-(4-aminopyrrolo[2,1-f][1,2,4]triazin-7-yl)-6-cyano-7-hydroxy-2-oxidotetrahydro-4H-furo[3,2-d][1,3,2]dioxaphosphinin-2-yl)oxy)methyl)benzoate (Compound 107)

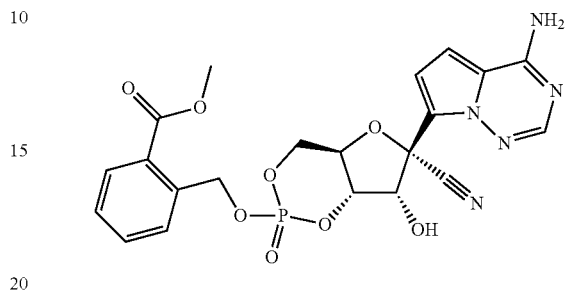

Compound 107 was prepared according to the method described in Scheme I from N,N,N',N'-tetraisopropyl-1-(2-(2-methyloxy)carbonylbenzyloxy)phosphanediamine and (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. [M−1]⁺ calculated for $C_{21}H_{20}N_5O_8P$: 500.09. Found: 500.0.

Example 8

Methyl 2-(((((4aR,6R,7R,7aR)-7-acetoxy-6-(4-aminopyrrolo[2,1-f][1,2,4]triazin-7-yl)-6-cyano-2-oxidotetrahydro-4H-furo[3,2-d][1,3,2]dioxaphosphinin-2-yl)oxy)methyl)benzoate (Compound 108)

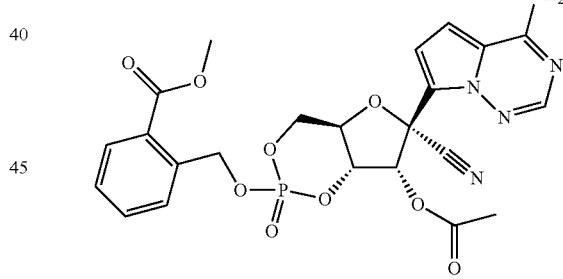

Compound 108 was prepared by standard acylation of Compound 107 with acetic anhydride in the presence of triethylamine. [M−1]⁺ calculated for $C_{23}H_{22}N_5O_9P$: 542.11. Found: 542.1.

Biological Examples

Examples the methods described herein include the following. It will be understood that the following are examples and that the method is not limited solely to these examples.

Example 9: Tissue Distribution Following Oral Administration of Reference Compound and the Disclosed Compounds IV Remdesivir (2 mg/kg), oral Remdesevir (5 mg/kg) and oral test compound (5 mg/kg) were administered to rats.

Oral administration was to fasted rats by oral gavage. Plasma concentrations of the metabolite nucleoside in circulation were determined by HPLC-UV, and the liver concentrations of the active triphosphate were measured by LC-MS using standard chromatography methods.

Figure 2:
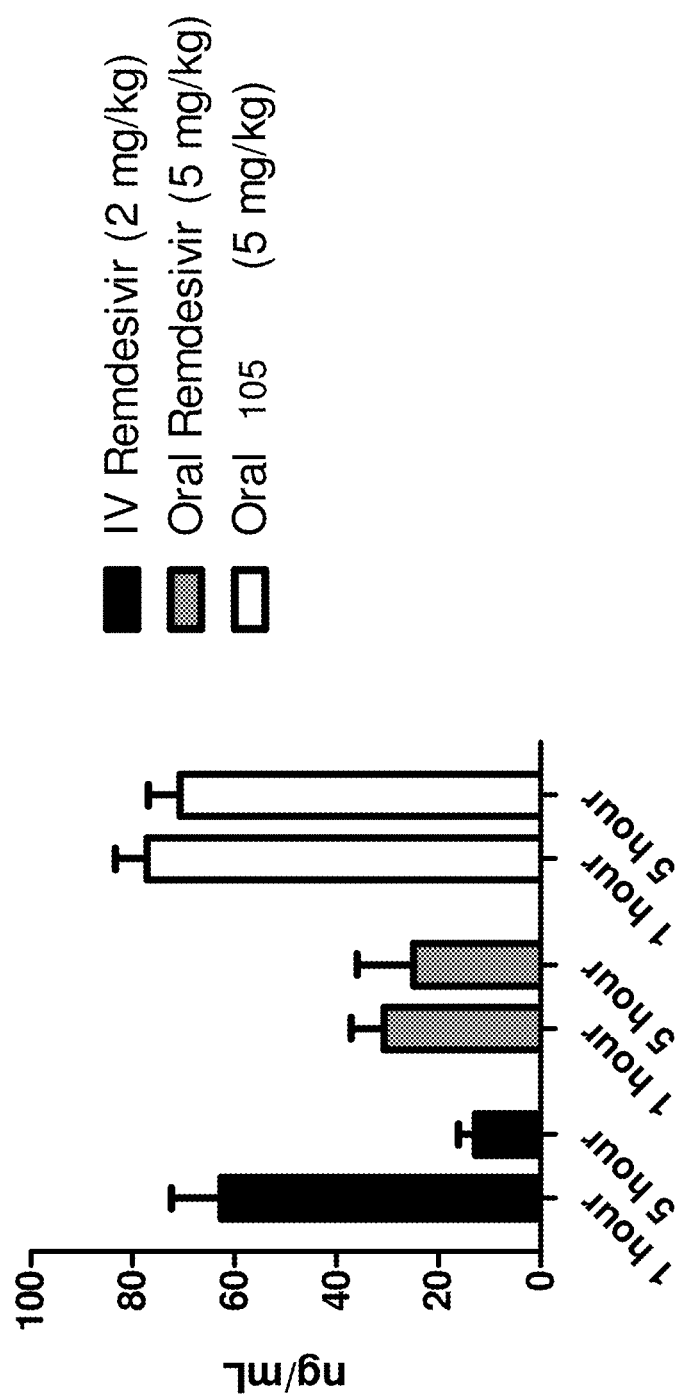
FIG. 2 is a graph showing the blood concentrations in rats of the corresponding nucleoside at selected time points after administration of IV Remdesivir, oral Remdesivir, or oral Compound 105.
Figure 3:
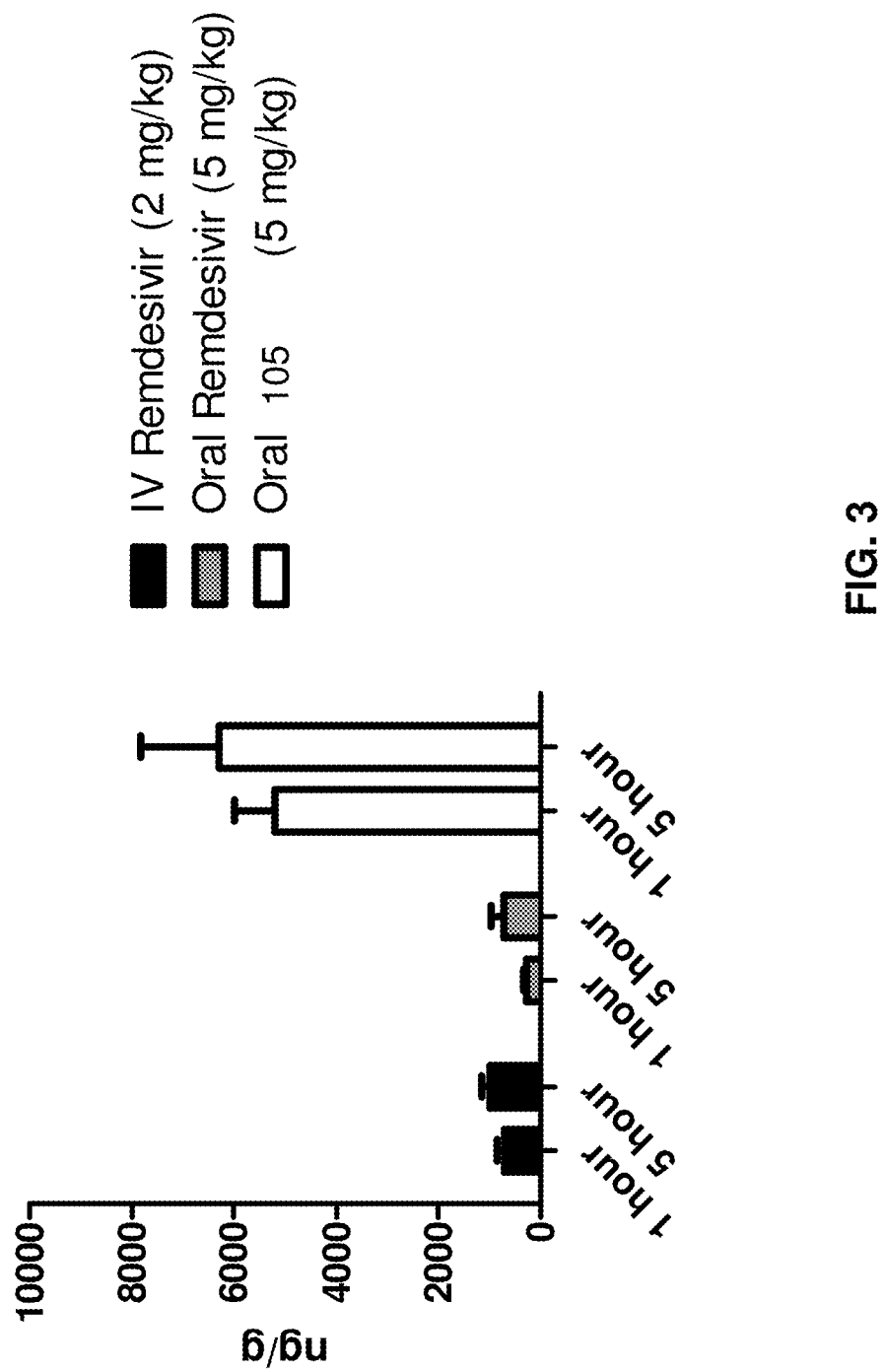
FIG. 3 is a graph showing the liver concentrations in rats of the corresponding triphosphate at selected time points after administration of IV Remdesivir, oral Remdesivir, or oral Compound 105.
Figure 4:
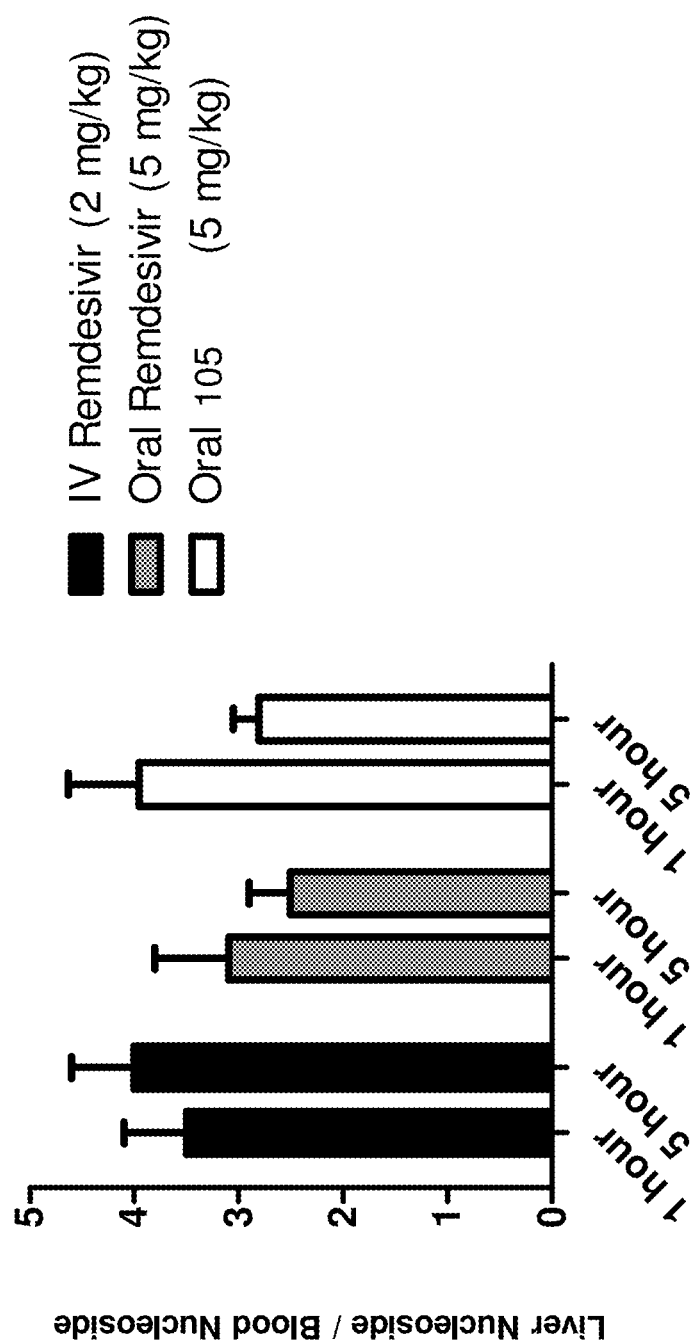
FIG. 4 is a graph showing the ratio of (concentration of corresponding nucleoside in the liver)/(concentration of corresponding nucleoside in the blood) in rats at selected time points after administration of IV Remdesivir, oral Remdesivir, or oral Compound 105.

FIG. 1 shows the results of a first study in which the up to 8-hour blood concentrations of the metabolite nucleoside were measured after administration of Compound 105 and reference compounds. FIG. 2 shows the results of a second study in which blood concentrations were measured after 1 and 5 hours. The results indicate that oral administration of Compound 105 resulted in greater than two times the exposure than oral administration of Remdesivir and greater exposure the IV administration of Remdesivir, particularly at longer times. FIG. 3 shows additional results from the second study in which the liver concentrations of the nucleoside triphosphate were measured after 1 and 5 hours. Compound 105 exhibited significantly greater liver exposure than either IV or oral Remdesivir although the ratio of liver vs. blood generated by Compound 105 remained the same as the ratio generated by Remdesivir. FIG. 4 is a graph showing the ratio of (concentration of corresponding nucleoside in the liver)/(concentration of corresponding nucleoside in the blood) after 1 and 5 hours from the second study.

Table 1 contains the blood and liver levels after 1 and 5 hours for a number of test compounds compared to oral Remdesivir. The results demonstrate that the test compounds provided much higher liver exposure than Remdesivir.

TABLE 1

Blood nucleoside (Nuc) and liver nucleoside triphosphate (NTP) levels at 1 and 5 hours after oral dosing of the compound.

| Compound | Blood Nuc level | | Liver NTP level | |
| --- | --- | --- | --- | --- |
| | at 1 hour | at 5 hours | at 1 hour | at 5 hours |
| Remdesivir | 1x | 1x | 1x | 1x |
| 101 | <1x | <1x | ≥2x | ≥2x |
| 105 | ≥2x* | ≥2x | ≥2x | ≥2x |
| 106 | ≥2x | ≥2x | ≥2x | ≥2x |

*≥2x means a concentration that is at least two-fold higher than the concentration generated by the reference compound.

Example 10: Tissue Distribution Following Inhalation Administration of Reference Compound and the Disclosed Compounds Remdesivir or the indicated test compound was administered at 2 mg/kg to rats by an inhalation route. The lung concentrations of the metabolite nucleoside and its triphosphate were measured by LC-MS using standard chromatography methods.

Figure 5:
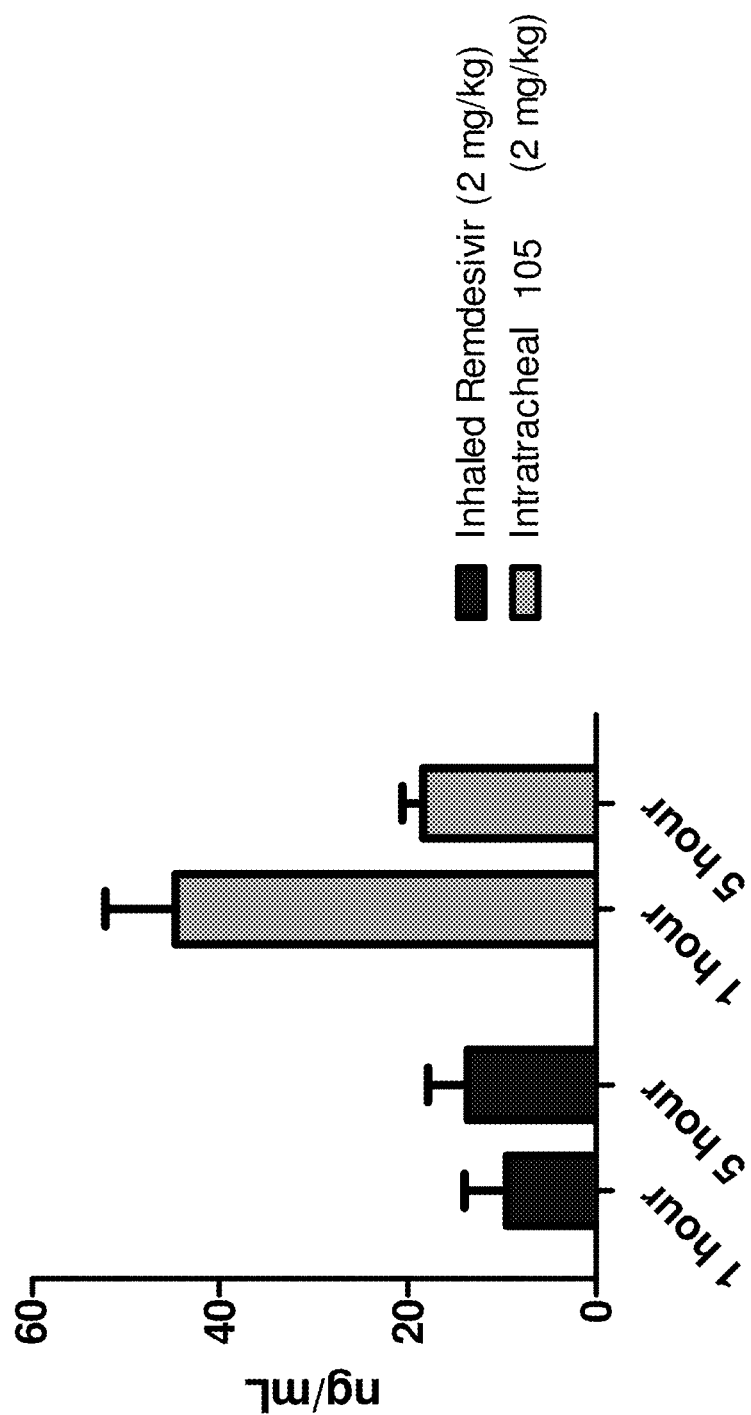
FIG. 5 is a graph showing the blood concentrations in rats of the corresponding nucleoside at selected time points after administration of inhaled Remdesivir or intratracheal Compound 105.
Figure 6:
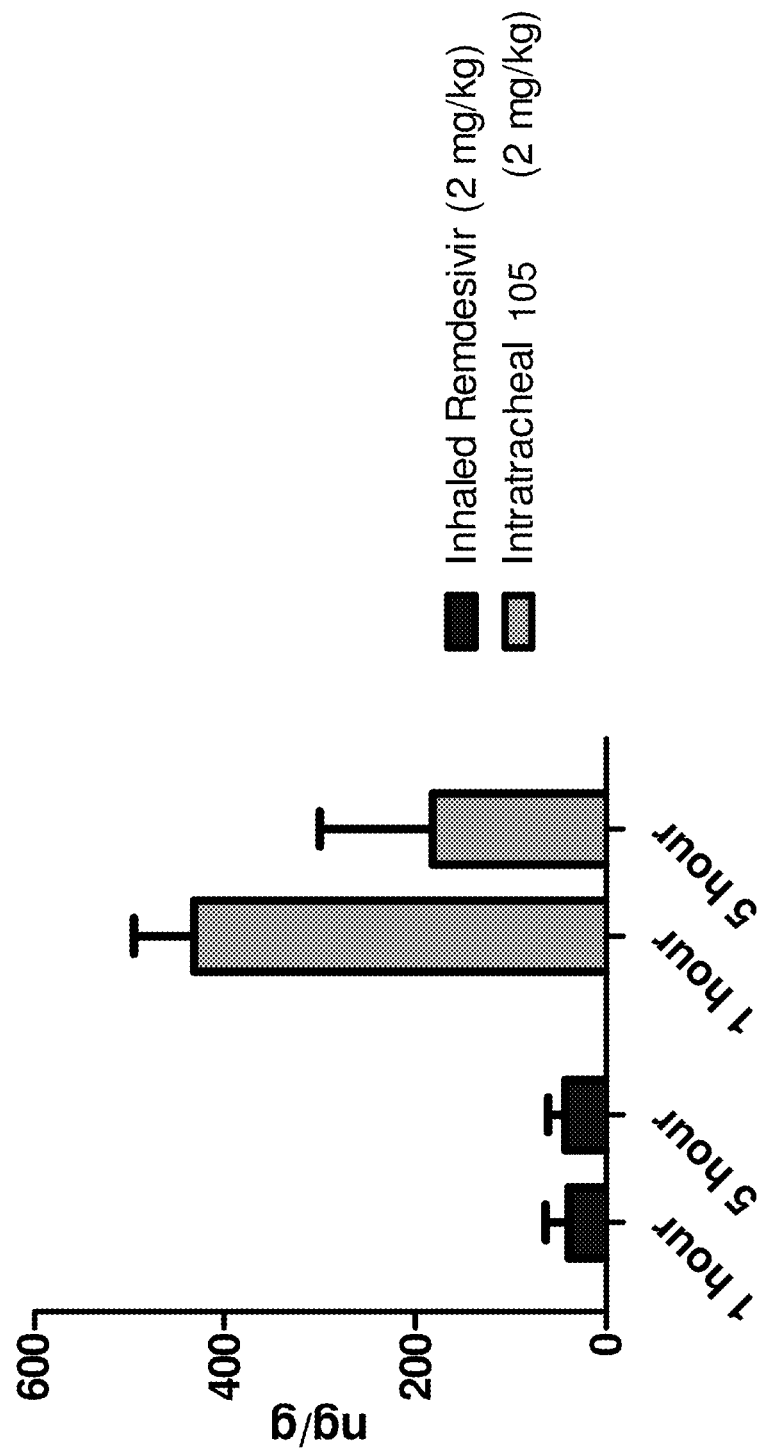
FIG. 6 is a graph showing the lung concentrations in rats of the corresponding nucleoside at selected time points after administration of inhaled Remdesivir or intratracheal Compound 105.
Figure 7:
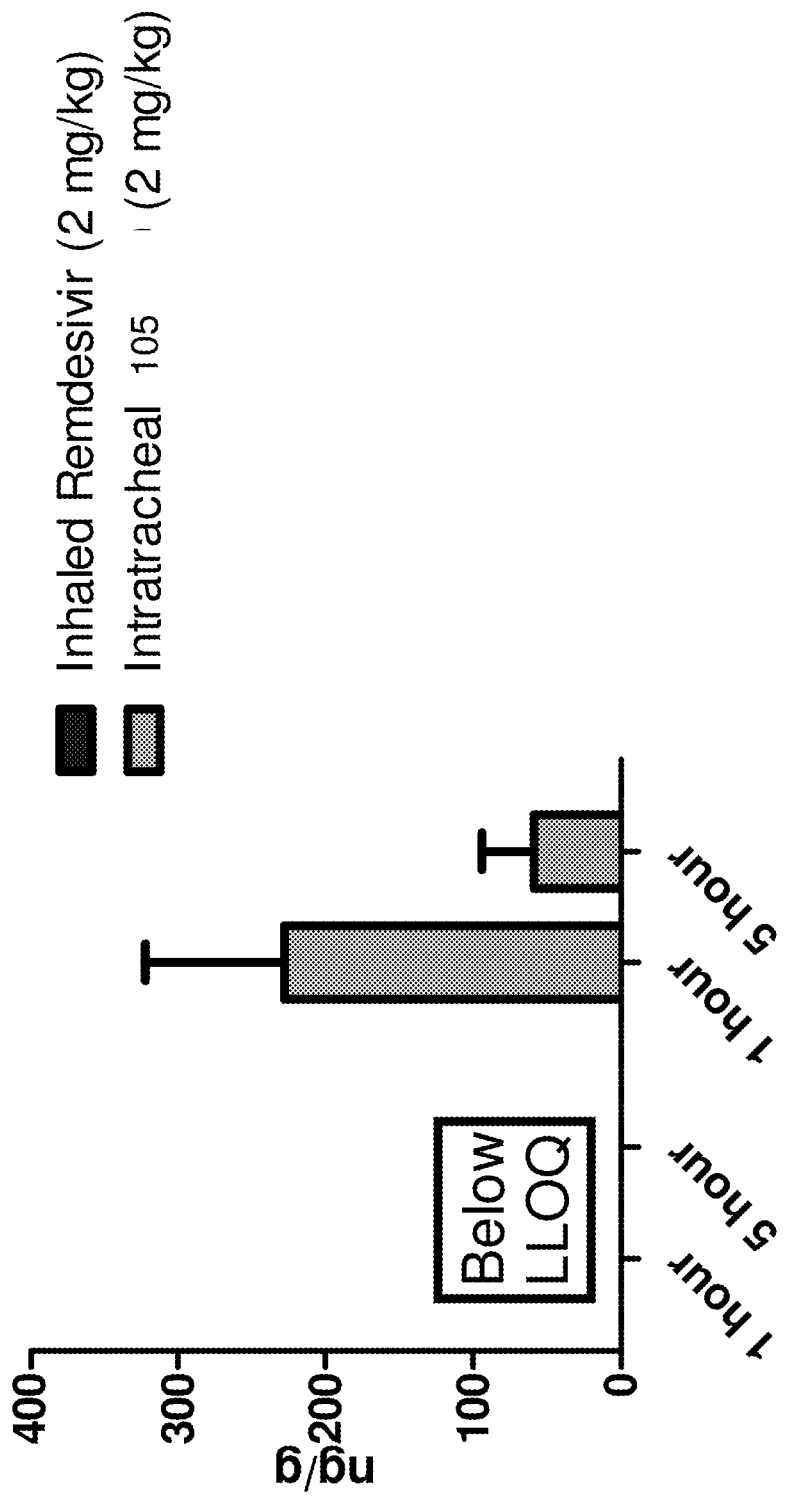
FIG. 7 is a graph showing the lung concentrations in rats of the corresponding triphosphate at selected time points after administration of inhaled Remdesivir or intratracheal Compound 105.

FIG. 5 shows the blood levels of the metabolite nucleoside at 1 and 5 hours after administration of Compound 105 and reference compound. Compound 105 provided greater exposure than Remdesivir. FIG. 6 shows the lung levels of the metabolite nucleoside. Compound 105 provided more than 4 times greater exposure than Remdesivir. FIG. 7 shows the nucleoside triphosphate levels in the lung. Remdesivir was below the level of quantitation, whereas Compound 105 provide significant lung exposure of the triphosphate.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15%, 10%, 5%, 3%, 1%, 0.1%, or otherwise. Similarly, in certain embodiments, the terms "generally perpendicular" and "substantially perpendicular" refer to a value, amount, or characteristic that departs from exactly perpendicular by less than or equal to 15%, 10%, 5%, 3%, 1%, 0.1%, or otherwise.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Although some embodiments and examples have been described, it should be understood that numerous and various modifications can be made without departing from the spirit of the invention.

What is claimed is:

1. A compound of Formula I:

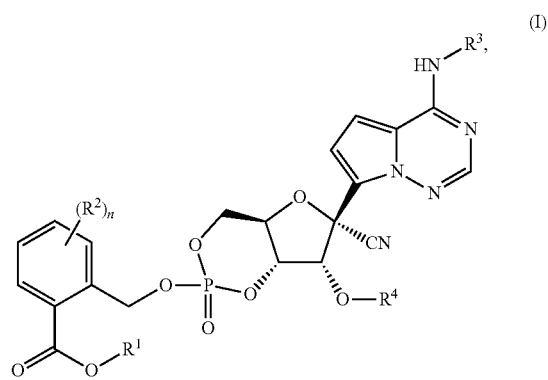

wherein:
R¹ is selected from the group consisting of H, an optionally substituted $C_1$-$C_{15}$ alkyl, an optionally substituted $C_3$-$C_{15}$ cycloalkyl, and an optionally substituted $C_2$-$C_{15}$ alkenyl;
R² is selected from the group consisting of halogen, an optionally substituted alkyl, and an optionally substituted alkyloxy;
R³ is selected from the group consisting of H, an optionally substituted acyl, and C-carboxy;
R⁴ is selected from the group consisting of H, an optionally substituted acyl, C-amido, and C-carboxy; and
n is 0, 1, 2, or 3;
or a stereoisomer or pharmaceutically acceptable salt thereof.

2. The compound of claim 1, wherein n is 1.
3. The compound of claim 1, wherein n is 0.
4. The compound of claim 1, wherein R³ is H.
5. The compound of claim 1, wherein R¹ is an optionally substituted $C_1$-$C_{15}$ alkyl.
6. The compound of claim 5, wherein R¹ is an unsubstituted $C_1$-$C_6$ alkyl.
7. The compound of claim 6, wherein R¹ is ethyl.
8. The compound of claim 6, wherein R¹ is n-propyl.
9. The compound of claim 6, wherein R¹ is i-propyl.
10. The compound of claim 6, wherein R¹ is methyl.
11. The compound of claim 1, wherein R⁴ is C-carboxy.
12. The compound of claim 1, wherein R⁴ is acyl.
13. The compound of claim 1, wherein the compound is selected from the group consisting of:

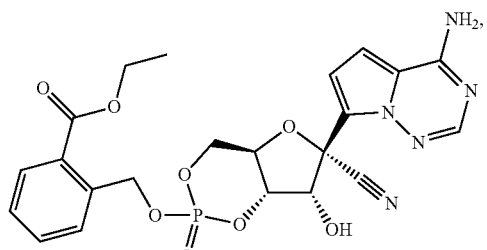

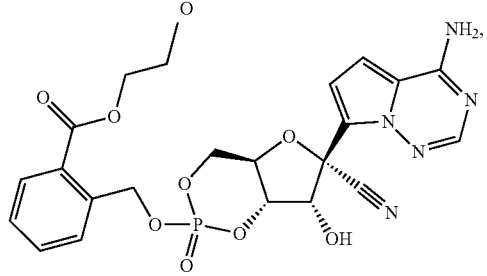

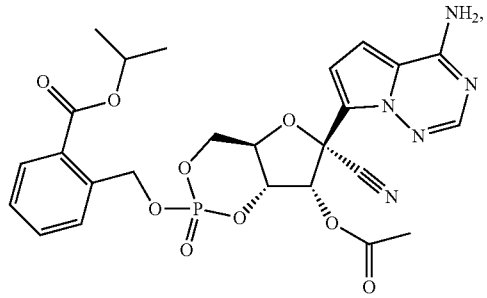

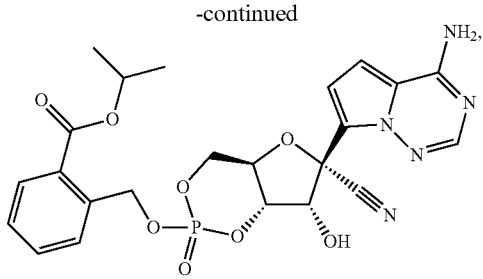

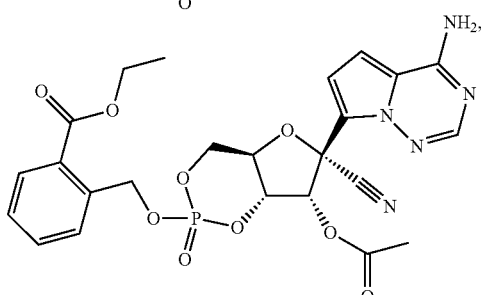

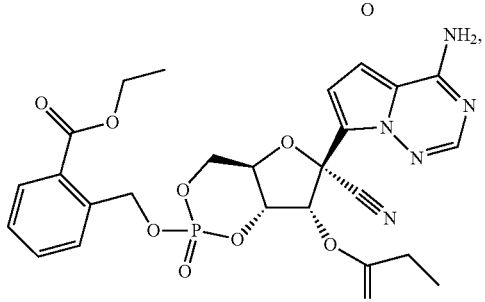

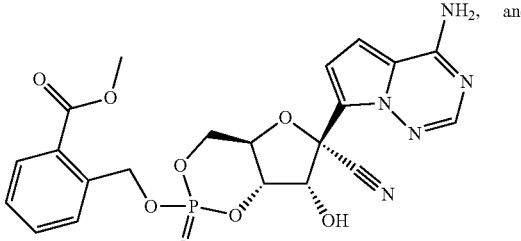

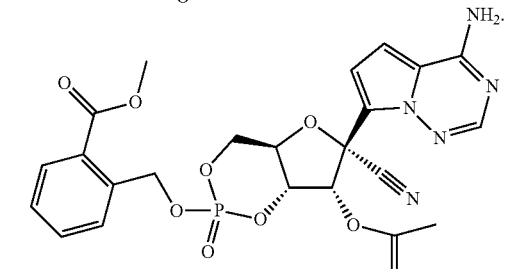

14. A method of treating a viral infection comprising administering an effective amount of a compound of claim 1 to a subject in need thereof.
15. The method of claim 14, wherein the subject is a mammal.
16. The method of claim 15, wherein the mammal is a human.
17. The method of claim 14, further comprising administering one or more additional therapeutic agents.

* * * * *